United States Patent
Coquerel et al.

(10) Patent No.: US 7,358,395 B2
(45) Date of Patent: Apr. 15, 2008

(54) CRYSTALLINE FORM V OF AGOMELATINE, A PROCESS FOR ITS PREPARATION AND PHARMACEUTICAL COMPOSITIONS CONTAINING IT

(75) Inventors: Gerard Coquerel, Boos (FR); Julie Linol, Rouen (FR); Jean-Claude Souvie, Le Havre (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/497,776

(22) Filed: Aug. 2, 2006

(65) Prior Publication Data
US 2006/0270877 A1   Nov. 30, 2006

Related U.S. Application Data

(60) Provisional application No. 60/705,049, filed on Aug. 3, 2005.

(30) Foreign Application Priority Data
Aug. 3, 2005  (FR) .................................. 05 08278

(51) Int. Cl.
*C07C 235/05*  (2006.01)
*A61K 31/165*  (2006.01)

(52) U.S. Cl. ....................... 564/172; 514/617
(58) Field of Classification Search ................ None
See application file for complete search history.

(56) References Cited

U.S. PATENT DOCUMENTS 5,194,614 A * 3/1993 Andrieux et al. .......... 544/400

2005/0164987 A1 * 7/2005 Barberich ..................... 514/58

FOREIGN PATENT DOCUMENTS

EP  0447285  9/1991
EP  1564202  8/2005

OTHER PUBLICATIONS

Tinant, B. et al., "N-[2-(7-methoxy-1-naphthyl)ethyl]acetamid E, a potent melatonin analog" ACTA Crystallographic section C. Crystal structure communications, vol. C50, No. 6, p. 907-910, 1994.
Depreux, P., et al., "Synthesis and structure-activity relationship of novel naphthalenic and bioisosteric amidic derivatives as melatonin receptor ligands" Journal of Medicinal Chemistry, vol. 37, No. 20, p. 3231-3239, 1994.
Chilman-Blair, K., et al., "Agomelatine antidepressant treatment of bipolar disorder melatonin agonist/5-HT20 antagonist" Durgs of the Future, vol. 28, No. 1, p. 7-13, 2003.
Preliminary Search Report for FR 0508278 of Jun. 26, 2006.

* cited by examiner

*Primary Examiner*—Sikarl A. Witherspoon
(74) *Attorney, Agent, or Firm*—Hueschen and Sage

(57) ABSTRACT

Crystalline form V of the compound of formula (I):

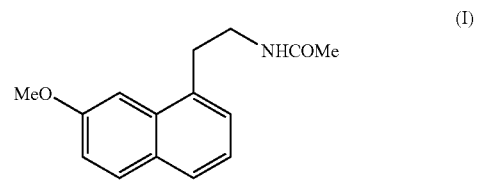

characterised by its powder X-ray diffraction diagram.

Medicinal products containing the same which are useful in the treatment of melatoninergic disorders.

6 Claims, No Drawings

CRYSTALLINE FORM V OF AGOMELATINE, A PROCESS FOR ITS PREPARATION AND PHARMACEUTICAL COMPOSITIONS CONTAINING IT

The present invention relates to a new crystalline form V of agomelatine, or N-[2-(7-methoxy-1-naphthyl)ethyl]acetamide, of formula (I):

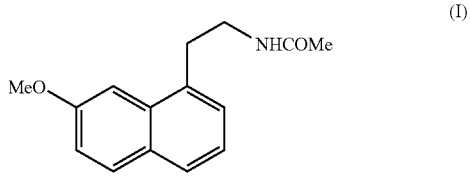

a process for its preparation and pharmaceutical compositions containing it.

BACKGROUND OF THE INVENTION

Agomelatine, or N-[2-(7-methoxy-1-naphthyl)ethyl]acetamide, has valuable pharmacological properties.

Indeed it has the double feature of being, on the one hand, an agonist of melatoninergic system receptors and, on the other hand, an antagonist of the $5\text{-HT}_{2C}$ receptor. Those properties confer activity in the central nervous system and, more especially, in the treatment of severe depression, seasonal affective disorders, sleep disorders, cardiovascular pathologies, pathologies of the digestive system, insomnia and fatigue resulting from jetlag, appetite disorders and obesity.

DESCRIPTION OF THE PRIOR ART

Agomelatine, its preparation and its therapeutic use have been described in European Patent Specification EP 0 447 285.

In view of the pharmaceutical value of this compound, it has been important to be able to obtain it with excellent purity, with well defined crystalline form, perfectly reproducible, which as a result exhibits valuable characteristics in terms of dissolution and formulation and sufficiently stable to allow its storage for long periods without particular requirements for temperature, light, humidity or oxygen level.

Patent Specification EP 0 447 285 describes the preparation of agomelatine in eight steps, starting from 7-methoxy-1-tetralone. However, that document does not specify the conditions for obtaining agomelatine in a form that exhibits those characteristics in a reproducible manner.

DETAILED DESCRIPTION OF THE INVENTION

The Applicant has now developed a new synthesis process that allows agomelatine to be obtained in a well defined, perfectly reproducible crystalline form that especially exhibits valuable characteristics for dissolution and formulation.

More specifically, the present invention relates to the crystalline form V of the compound of formula (I), characterised by the following powder X-ray diffraction diagram, measured using a Siemens D5005 diffractometer (copper anticathode) and expressed in terms of inter-planar distance d, Bragg's angle 2 theta, intensity and relative intensity (expressed as a percentage of the most intense ray):

| 2-Theta (°) exp. | d (Å) exp. | Intensité (%) |
|---|---|---|
| 9.84 | 8.979 | 17 |
| 12.40 | 7.134 | 15 |
| 13.31 | 6.646 | 19 |
| 15.14 | 5.848 | 18 |
| 15.98 | 5.543 | 18 |
| 16.62 | 5.329 | 19 |
| 17.95 | 4.939 | 100 |
| 18.88 | 4.697 | 65 |
| 20.49 | 4.332 | 24 |
| 20.99 | 4.228 | 34 |
| 23.07 | 3.852 | 39 |
| 23.44 | 3.792 | 36 |
| 24.28 | 3.663 | 58 |
| 25.10 | 3.545 | 19 |
| 26.02 | 3.422 | 15 |
| 26.82 | 3.322 | 19 |
| 27.51 | 3.239 | 16 |

The invention relates also to a process for the preparation of the crystalline form V of the compound of formula (I), which process is characterised in that agomelatine is subjected to a mechanical grinding which is said to be "of high energy".

In the crystallisation process according to the invention it is possible to use the compound of formula (I) obtained by any process.

The invention relates also to another process for the preparation of the crystalline form V of the compound of formula (I), which process is characterised in that agomelatine is heated until complete melting, then immediately put at room temperature and simultaneously a small quantity of crystalline form V of compound of formula (I) freshly prepared is added, and the mixture is cooled until crystallisation is complete.

Preferably, in that second crystallisation process according to the invention, agomelatine will be melted at 110° C.

The amount of crystalline form V added in that second process according to the invention will be preferably contained between 1/100 and 1/50 of agomelatine weight.

In that second crystallisation process according to the invention, it is possible to use the compound of formula (I) obtained by any process.

An advantage of obtaining that crystalline form is that it allows the preparation of pharmaceutical formulations having a consistent and reproducible composition, which as a result exhibits valuable characteristics in terms of dissolution which is especially advantageous when the formulations are to be used for oral administration.

A pharmacological study of the form V so obtained has demonstrated that it has substantial activity in respect of the central nervous system and in respect of microcirculation, enabling it to be established that the crystalline form V of agomelatine is useful in the treatment of stress, sleep disorders, anxiety, severe depression, seasonal affective disorders, cardiovascular pathologies, pathologies of the digestive system, insomnia and fatigue due to jetlag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the crystalline V form of agomelatine can be used in the treatment of sexual dysfunction, that it has ovulation-inhibiting and immunomodulating properties and that it lends itself to use in the treatment of cancers.

The crystalline form V of agomelatine will preferably be used in the treatment of severe depression, seasonal affective disorders, sleep disorders, cardiovascular pathologies, insomnia and fatigue due to jetlag, appetite disorders and obesity.

The invention relates also to pharmaceutical compositions comprising as active ingredient the crystalline form V of agomelatine together with one or more appropriate inert, non-toxic excipients. Among the pharmaceutical compositions according to the invention there may be mentioned, more especially, those which are suitable for oral, parenteral (intravenous or subcutaneous) or nasal administration, tablets or dragees, granules, sublingual tablets, gelatin capsules, lozenges, suppositories, creams, ointments, dermal gels, injectable preparations, drinkable suspensions and disintegrable pastes.

The useful dosage can be adapted according to the nature and the severity of the disorder, the administration route and the age and weight of the patient. The dosage varies from 0.1 mg to 1 g per day in one or more administrations.

The Examples below illustrate the invention but do not limit it in any way.

EXAMPLE 1

Crystalline form V of N-[2-(7-Methoxy-1-naphthyl)ethyl]acetamide 100 g of N-[2-(7-Methoxy-1-naphthyl)ethyl]acetamide are put in a mechanical grinder of the vario-planetary mill type for about 6 hours and the solid obtained is characterised by the following powder X-ray diffraction diagram, measured using a Siemens D5005 diffractometer (copper anticathode) and expressed in terms of inter-planar distance d, Bragg's angle 2 theta, intensity and relative intensity (expressed as a percentage of the most intense ray):

| 2-Theta (°) exp. | d (Å) exp. | Intensité (%) |
|---|---|---|
| 9.84 | 8.979 | 17 |
| 12.40 | 7.134 | 15 |
| 13.31 | 6.646 | 19 |
| 15.14 | 5.848 | 18 |
| 15.98 | 5.543 | 18 |
| 16.62 | 5.329 | 19 |
| 17.95 | 4.939 | 100 |
| 18.88 | 4.697 | 65 |
| 20.49 | 4.332 | 24 |
| 20.99 | 4.228 | 34 |
| 23.07 | 3.852 | 39 |
| 23.44 | 3.792 | 36 |
| 24.28 | 3.663 | 58 |
| 25.10 | 3.545 | 19 |
| 26.02 | 3.422 | 15 |
| 26.82 | 3.322 | 19 |
| 27.51 | 3.239 | 16 |

EXAMPLE 2

Crystalline form V of N-[2-(7-Methoxy-1-naphthyl)ethyl]acetamide 4 g of N-[2-(7-Methoxy-1-naphthyl)ethyl]acetamide are put in a ventilated incubator at 110° C. After 1 hour at 110° C., the product is immediately placed at room temperature and seeded with 0.05 g of crystalline form V of N-[2-(7-Methoxy-1-naphthyl)ethyl]acetamide structurally pure obtained by mechanical grinding of high energy. After 5 minutes, the crystallisation is complete and the solid obtained is characterised by the following powder X-ray diffraction diagram, measured using a Siemens D5005 diffractometer (copper anticathode) and expressed in terms of inter-planar distance d, Bragg's angle 2 theta, intensity and relative intensity (expressed as a percentage of the most intense ray):

| 2-Theta (°) exp. | d (Å) exp. | Intensité (%) |
|---|---|---|
| 9.84 | 8.979 | 17 |
| 12.40 | 7.134 | 15 |
| 13.31 | 6.646 | 19 |
| 15.14 | 5.848 | 18 |
| 15.98 | 5.543 | 18 |
| 16.62 | 5.329 | 19 |
| 17.95 | 4.939 | 100 |
| 18.88 | 4.697 | 65 |
| 20.49 | 4.332 | 24 |
| 20.99 | 4.228 | 34 |
| 23.07 | 3.852 | 39 |
| 23.44 | 3.792 | 36 |
| 24.28 | 3.663 | 58 |
| 25.10 | 3.545 | 19 |
| 26.02 | 3.422 | 15 |
| 26.82 | 3.322 | 19 |
| 27.51 | 3.239 | 16 |

EXAMPLE 3

Pharmaceutical Composition

Formulation for the preparation of 1000 tablets each containing a dose of 25 mg:

| | |
|---|---|
| Compound of Example 1 or 2 | 25 g |
| Lactose monohydrate | 62 g |
| Magnesium stearate | 1.3 g |
| Maize starch | 26 g |
| Maltodextrines | 9 g |
| Silica, colloidal anhydrous | 0.3 g |
| Sodium starch glycolate type A | 4 g |
| Stearic acid | 2.6 g |

EXAMPLE 4

Pharmaceutical Composition

Formulation for the preparation of 1000 tablets each containing a dose of 25 mg:

| | |
|---|---|
| Compound of Example 1 or 2 | 25 g |
| Lactose monohydrate | 62 g |
| Magnesium stearate | 1.3 g |
| Povidone | 9 g |
| Silica, colloidal anhydrous | 0.3 g |
| Sodium cellulose glycolate | 30 g |
| Stearic acid | 2.6 g |

We claim:

1. A crystalline form V of the compound of formula (I):

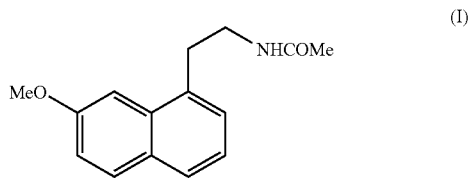

(I)

wherein the compound exhibits essentially the following powder X-ray diffraction diagram, measured using a diffractometer (copper anticathode) and expressed in terms of inter-planar distance d (expressed in Å), Bragg's angle 2 theta (expressed in degrees), intensity and relative intensity (expressed as a percentage with respect to the most intense ray):

| 2-Theta (°) exp. | d (Å) exp. | Intensité (%) |
|---|---|---|
| 9.84 | 8.979 | 17 |
| 12.40 | 7.134 | 15 |
| 13.31 | 6.646 | 19 |
| 15.14 | 5.848 | 18 |
| 15.98 | 5.543 | 18 |
| 16.62 | 5.329 | 19 |
| 17.95 | 4.939 | 100 |
| 18.88 | 4.697 | 65 |
| 20.49 | 4.332 | 24 |
| 20.99 | 4.228 | 34 |
| 23.07 | 3.852 | 39 |
| 23.44 | 3.792 | 36 |
| 24.28 | 3.663 | 58 |
| 25.10 | 3.545 | 19 |
| 26.02 | 3.422 | 15 |
| 26.82 | 3.322 | 19 |
| 27.51 | 3.239 | 16. |

2. A process for the preparation of the crystalline form V of the compound of formula (I) of claim 1, wherein agomelatine is subjected to high energy mechanical grinding.

3. A process for the preparation of the crystalline form V of the compound of formula (I) of claim 1, wherein agomelatine is heated until completely melted, then immediately placed at room temperature and simultaneously a small quantity of crystalline form V of compound of formula (I) is added, and the mixture is cooled until crystallisation is complete.

4. A pharmaceutical composition comprising as active ingredient an effective amount of crystalline form V of the compound of claim 1, in combination with one or more pharmaceutically acceptable, inert, non-toxic carriers.

5. A method for treating a living animal body, including a human, afflicted with disorders of the melatoninergic system comprising the step of administering to the living animal body, including a human, an amount of crystalline form V of the compound of claim 1, which is effective for the alleviation of the disorder.

6. A method for treating a living animal body, including a human, afflicted with sleep disorders, stress, anxiety, seasonal affective disorders or severe depression, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, migraine, memory loss, Alzheimer's disease, and cerebral circulation disorders, comprising the step of administering to the living animal body, including a human, an amount of crystalline form V of the compound of claim 1, which is effective for the alleviation of the disorder.

* * * * *

UNITED STATES PATENT AND TRADEMARK OFFICE
CERTIFICATE OF CORRECTION

PATENT NO. : 7,358,395 B2
APPLICATION NO. : 11/497776
DATED : April 15, 2008
INVENTOR(S) : Gerard Coquerel et al.

It is certified that error appears in the above-identified patent and that said Letters Patent is hereby corrected as shown below:

Title Page, Assignee: "Les Laboratories Servier" should be -- Les Laboratoires Servier --.

Signed and Sealed this

Twenty-fifth Day of May, 2010

David J. Kappos
*Director of the United States Patent and Trademark Office*